United States Patent [19]

Axelgaard et al.

[11] Patent Number: 5,038,796
[45] Date of Patent: * Aug. 13, 1991

[54] ELECTRICAL STIMULATION ELECTRODE WITH IMPEDANCE COMPENSATION

[75] Inventors: Jens Axelgaard, Fallbrook; Theodore Grussing, Huntington Beach, both of Calif.

[73] Assignee: Axelgaard Manufacturing Co., Ltd., Fallbrook, Calif.

[*] Notice: The portion of the term of this patent subsequent to Sep. 18, 2004 has been disclaimed.

[21] Appl. No.: 337,389

[22] Filed: Apr. 13, 1989

Related U.S. Application Data

[63] Continuation-in-part of Ser. No. 98,613, Sep. 18, 1987, Pat. No. 4,867,166, which is a continuation-in-part of Ser. No. 745,018, Jun. 14, 1985, Pat. No. 4,722,354.

[51] Int. Cl.$^5$ ............................................. A61N 1/04
[52] U.S. Cl. ..................................... 128/798; 128/802
[58] Field of Search ............... 128/639, 640, 641, 644, 128/798, 799, 802, 803

[56] References Cited

U.S. PATENT DOCUMENTS

| | | | |
|---|---|---|---|
| 683,098 | 9/1901 | Baecker | 128/783 |
| 1,989,282 | 1/1935 | Kimble et al. | 128/798 |
| 3,972,329 | 8/1976 | Kaufman | 128/2.06 E |
| 3,993,049 | 11/1976 | Kater | 128/2.06 E |
| 4,066,078 | 1/1978 | Berg | 128/2.06 E |
| 4,092,985 | 6/1978 | Kaufman | 128/303.13 |
| 4,166,465 | 9/1979 | Esty et al. | 128/303.13 |
| 4,213,463 | 7/1980 | Osenkarski | 128/639 |
| 4,239,046 | 12/1980 | Ong | 128/640 |
| 4,243,051 | 1/1981 | Wittemann | 128/798 |
| 4,243,052 | 1/1981 | Bailey | 128/798 |
| 4,274,420 | 6/1981 | Hymes | 128/641 |
| 4,300,575 | 11/1981 | Wilson | 128/798 |
| 4,391,278 | 7/1983 | Cahalan et al. | 128/640 |
| 4,422,461 | 12/1983 | Glumac | 128/798 |
| 4,458,696 | 7/1984 | Larimore | 128/798 |
| 4,867,166 | 9/1989 | Axelgaard et al. | 128/640 |
| 4,893,626 | 1/1990 | Henley et al. | 128/798 |

FOREIGN PATENT DOCUMENTS

| | | |
|---|---|---|
| 51031 | 6/1911 | Austria . |
| 372002 | 8/1983 | Austria . |
| 2059 | 5/1979 | European Pat. Off. . |
| 29245 | 5/1981 | European Pat. Off. . |
| 2023919 | 11/1971 | Fed. Rep. of Germany . |
| 2209430 | 9/1973 | Fed. Rep. of Germany . |
| 2552197 | 5/1976 | Fed. Rep. of Germany . |
| 750222 | 8/1933 | France . |
| 1036328 | 8/1983 | U.S.S.R. . |
| 2045088 | 10/1980 | United Kingdom . |

Primary Examiner—Lee S. Cohen
Assistant Examiner—John P. Lacyk
Attorney, Agent, or Firm—Walter A. Hackler

[57] ABSTRACT

A flexible transcutaneous electrical nerve and/or muscle stimulation electrode is provided which utilizes a conductive material, preferably a conductive fabric, and electrical shunt means disposed along the conductive material for causing more uniform resistivity between any two equally spaced apart points on the conductive material than without the electrical shunt means. Further adjustment of the electrical conductivity may also be achieved by varying the conductivity of individual fibers utilized in the conductive fabric.

34 Claims, 4 Drawing Sheets

FIG. 17. 1/2" PROBE MAP OF 3"x5" OVAL WOVEN - WIRE: 1.2"

FIG. 18. 1/2" PROBE MAP OF 3"x5" OVAL JERSEY KNIT - WIRE: 4"

ELECTRICAL STIMULATION ELECTRODE WITH IMPEDANCE COMPENSATION

This application is a Continuation-In-Part U.S. Patent Application Serial No. 098,613 filed Sept. 18, 1987, now U.S. Pat. No. 4,867,166, issued Sept. 19, 1989, which was a Continuation-In-Part of U.S. patent application Ser. No. 745,018, filed June 14, 1985, now U.S. Pat. No. 4,722,354, issued Feb. 2, 1988.

The present invention generally relates to electrodes and, more particularly, to electrodes suitable for transcutaneous nerve and/or muscle stimulation.

Continued development of electrical medical devices has produced a need for a variety of electrodes.

Although many of these electrodes have, as a design objective, good electrical signal transmission between a patient's skin surface and electrical leads interconnected with a device, each has specific requirements dependent upon the type of apparatus for which it is to be used.

As an example, electrocardiograph (EKG) and electroencephalograph (EEG) machines are primarily monitoring type devices which require small contact surfaces, or area, with the patient's skin.

On the other hand, transcutaneous electric nerve stimulation (TENS), and muscle stimulation devices require relatively large skin surface contact to effect such nerve and muscle stimulation.

Transcutaneous electrical nerve stimulation is useful, for example, in post-operative and chronic pain control, while muscle stimulation is useful, for example, in maintaining and development of muscle tissue. Electrodes suitable for use in nerve and muscle stimulation preferably provide a uniform electrical coupling across the skin electrode interface As hereinbefore noted, electrodes suitable for nerve and/or muscle stimulation may be relatively large having dimensions of several inches or more.

Because nerve and/or muscle stimulation causes muscle contraction, a considerable amount of skin movement is associated therewith.

Additionally, perspiration from the skin is more likely to loosen or disrupt the electrode because of its large size. As should be apparent, the larger the electrode, the longer the evaporation path, or distance, the perspiration occurring at the center regions of the electrode must travel in order to evaporate, or be released to the atmosphere.

It has been found that prior art electrodes which have been secured to the surface of a patient's skin with medical adhesive tape, or the like, have a tendency to lift off from the skin because of perspiration and movement of the patient's skin during treatment.

Because an electrode suitable for nerve and/or muscle stimulation must provide for an electrical signal to be distributed over the entire surface of the electrode, the electrode must necessarily be conductive.

Prior art electrodes have utilized a number of conductive elements, such as carbon impregnated rubber and vinyl, as well as metallic foils.

However, a useful electrode must be flexible in order to accommodate relative movement of the patient's skin therebeneath, as hereinabove-described.

Because nerve and muscle stimulation electrodes may be utilized over a long period of time, as may be necessary in connection with sports injuries, the electrode must be compatible with the skin and flex therewith.

Insufficient flexing of the electrode can result in severe irritation of the patient's skin and electrical "hot spots" due to uneven electrode-skin contact, which manifests itself in a rash and a burning sensation.

The sensation of burning may be sensed by the patient within a few minutes after application of electrical signals during nerve and/or muscle stimulation, while the rash conditions generally take a longer period of time to develop.

It has been found that the use of prior art electrodes in nerve and/or muscle stimulation results in a skin rash in up to 25% to 35% of the people undergoing treatment.

An additional problem associated with the necessary stretchability of electrodes utilized in nerve and/or muscle stimulation procedures is that while the electrode must be able to flex, or stretch, in order to accommodate skin movement during treatment, the conductivity of the electrode should not be interrupted, or distorted, due to the stretching of the electrode.

Prior art electrodes have compromised the flexibility of the electrode in an effort to provide uniform current densities over the entire contact area of the electrode. These electrodes typically utilize a metallic mesh, or foil, to provide contactivity of the electrode and utilize a conductive gel between the electrode and the patient's skin in order to accommodate movement therebetween.

There is, however, relative movement between the relatively rigid electrode and the skin, which is accommodated for by the gel. This relative movement oftentimes causes the gel to move from beneath the conductive portion of the electrode, thereby limiting the useful life of the electrode on the skin.

In addition, this relative motion between the skin and the electrode does not provide for the maintenance of the position of the electrode relative to the nerve and/or muscle being stimulated.

Precision positioning of the electrode is, of course, performed by a physician, or the like, knowledgeable in the treatment method. Inaccurate placement of the electrode, or slipping of the electrode from its intended position, may significantly reduce the beneficial effects of the treatment.

Hence, there is a need for a flexible electrode for use with electrical stimulation devices which adheres well to the patient's skin, is easily removed therefrom, and is able to move with the patient's skin in order to ensure proper continuous placement of the electrode relative to nerve or muscle tissue being stimulated, as well as providing long-term continuous electrical connection therewith without irritation of the skin or discomfort to the patient under treatment. The electrode of the present invention fulfills these needs.

SUMMARY OF THE INVENTION

A flexible transcutaneous electrical nerve and/or muscle stimulation electrode in accordance with the present invention includes a conductive material for directly coupling electrical signals to a patient's skin. In addition, the conductive material may comprise a conductive fabric having conductive fiber means for enabling the conductive fabric to be stretched. The conductive fabric comprises an array of conductive fibers with interstitial areas therebetween and has a different electrical resistivity in different directions therealong.

Flexible conductive adhesive means are provided and disposed within the interstitial areas and on one side of the conductive fabric for adhering the flexible transcutaneous electrical nerve and/or muscle stimulation electrode to the skin of a patient and providing an electrical conducting contact therebetween. Electrical shunt means are provided and disposed along the conductive fabric for causing more uniform resistance between any two equally spaced points on said conductive fabric than without the electrical shunt.

Interconnection with an electrical stimulation device is provided by means of an electrical lead wire which is interconnected with the electrical shunt means and a non-conductive sheet is disposed on the conductive fabric for preventing undesired electrical electrical contact therewith.

More particularly, the flexible stimulation electrode according to the present invention may include a conductive fabric comprising a knit of conductive fibers having a higher resistivity along a longitudinal direction of knit than along a transverse direction of knit and the resistivity along the longitudinal direction may be up to 20 times the resistivity along the transverse direction of knit. The shunt, in accordance with the present invention, may include a single wire or a plurality of strands.

In one embodiment of the present invention, the electrical shunt includes a plurality of strands disposed in a vein-like manner having a dichotomous venation.

Another embodiment of the present invention, the electrical shunt may include a plurality of strands disposed in a vein-like manner having a pinnate reticulate venation.

And yet, another embodiment of the present invention the electrical shunt may include a plurality of strands disposed in a vein-like manner having a palmate reticulate venation.

Still another embodiment of the present invention may include electrical shunt including a plurality of strands disposed in a vein-like manner having a parallel venation. The electrical shunt means may be disposed on an opposite side of the conductive fabric and held against the opposite side in an electrically conductive manner by the flexible solid conductive adhesive disposed in the interstitial areas.

Means may also be provided defining an overall shape of the conductive fabric for enabling improved conformity around and/or between body extremities than a conductive fabric having a shape selected from the group of square, rectangular and round. This overall shape results in a different electrical resistance between any two opposing points along a perimeter of the conductive fabric. In this embodiment, electrical shunt means are provided and disposed along the conductive fabric for equalizing the electrical resistance between any two points along the perimeter of the conductive fabric.

DESCRIPTION OF THE DRAWINGS

The advantages and features of the present invention will be better understood by the following description and drawings in which:

FIG. 15 is a probe map of the electrode shown in FIG. 14a;

DETAILED DESCRIPTION

Figures 1, 2, 3:
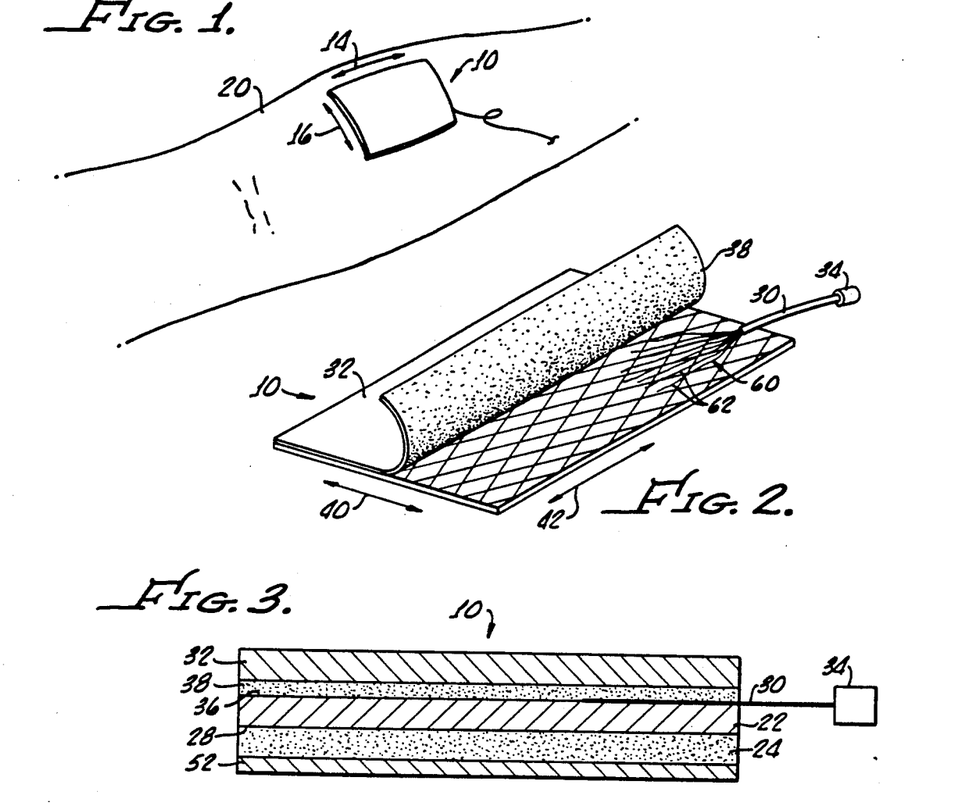
FIG. 1 is a perspective view of a flexible transcutaneous electrical nerve and/or muscle stimulation electrode in accordance with the present invention showing its disposition on a patient's skin.
FIG. 2 is a perspective view of the stimulation electrode with a portion of a non-conductive sheet thereof peeled back to show an electrical lead wire therein.
FIG. 3 is a cross-sectional view of the transcutaneous electrical nerve and/or muscle stimulation electrode generally showing conductive fabric, a flexible conductive adhesive, electrical lead wire, non-conductive sheet and a pressure sensitive adhesive.

Turning now to FIGS. 1 and 2, there is shown, in perspective view, a flexible transcutaneous electrical nerve and/or muscle stimulation electrode 10 in accordance with the present invention.

As shown in FIG. 1 and hereinafter described in greater detail, the electrode 10 is flexible in two directions, as indicated by arrows 14, 16, while in place on a patient's limb 20, or body, not shown. As more clearly shown in FIG. 3, the electrode 10 includes a stretchable conductive fabric 22, flexible conductive adhesive 24, which is disposed on one side 28 of the conductive fabric 22 for adhering the flexible transcutaneous electrical nerve and/or muscle stimulation electrode 10 to the skin of a patient (not shown in FIG. 3) and an electrical lead wire 30 interconnected with the conductive fabric 22, as hereinafter described, for providing electrical signals to the conductive fabric 22 when interconnected with an electrical stimulation device, not shown, by means of a connector 34, or the like.

In addition, a non-conductive sheet, such as a flexible plastic 32 disposed on another side 36 of the conductive fabric 22 by means of a pressure sensitive adhesive 38, provides means for preventing undesired electrical contact with the conductive fabric 22, as may occur during wearing of the device.

It should be appreciated that the conductive fabric 22 must be isolated from outside objects and other areas of the patient's skin in order to preferentially couple electrical signals into the patient's body where prescribed by an attending physician.

Figure 4:
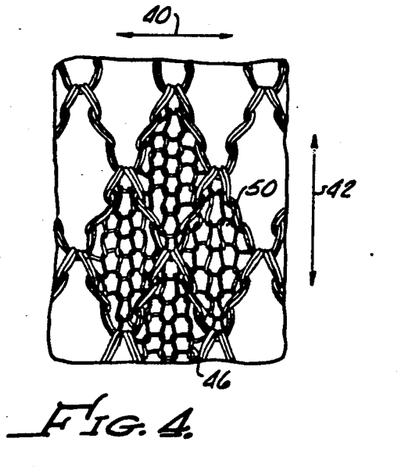
FIG. 4 is an enlarged view of the conductive fabric utilized in the present invention generally showing a honeycomb latch needle knit.
Figure 5:
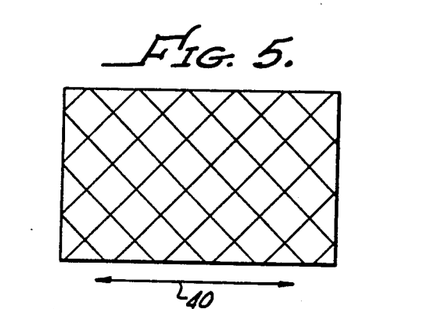
FIG. 5 is an illustration of the conductive fabric utilized in the present invention stretched in a transverse direction.
Figure 6:
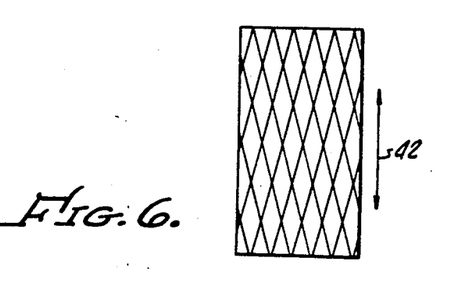
FIG. 6 is an illustration of the conductive fabric utilized in the present invention stretched in a longitudinal direction.

It has been found that a knit fabric, preferably a one-quarter-inch honeycomb latch needle knit fabric, as depicted in FIG. 4, provides for a fabric which may be stretched up to about 100 percent greater than a first original conductive fiber dimension in the direction of stretch, see arrow 40 and FIG. 5, and up to about 50 percent greater than a second original fabric dimension in a second direction of stretch, see arrow 42 and FIG. 6, without loss of conductivity of the fabric. Knits of this nature are commercially available from knitters, such as, for example, Paragon West Knitting Mill in Anaheim Hills, Calif.

Figure 7:
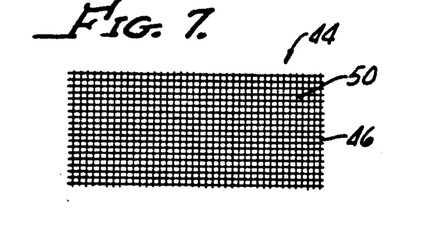
FIG. 7 is an illustration of woven conductive fabric suitable for use in the present invention

Woven fabrics, such as illustrated in FIG. 7, are also suitable if less stretch is required, as may be the case when the electrode is utilized on less curvature portions of the body, such as the back.

The conductivity of the fabric is provided by the individual conductive fibers 46. It has been found that a conductive fiber No. BK50/2 manufactured by Bekaert of Belgium, which includes a blend of 20 percent 316 stainless steel and 80 percent of polyester when latch needle honeycomb knitted to a density of about 2.5 pounds per square yard, produces a conductive double-stretch knit which is particularly suitable for transcutaneous nerve and/or muscle stimulation electrodes.

The double-stretch nature of the knit fabric, when incorporated into the electrode of the present invention, as hereindescribed, provides for an electrode which is contourable to the shape of a patient's body or limb.

This is particularly important with relatively large stimulation/electrodes in accordance with the present invention. The electrode 10 may have dimensions in the range of, for example, 2 inches by 3 inches, hence, the electrode must be "fitted" by stretching of the electrode 10 to the skin 20 of a patient in order to provide a uniform contact therebetween.

It is particularly important that the electrode 10 and, of course, the conductive fabric 22, do not degrade during constant and repetitious movement and stretching thereof, as the electrical signals activate muscles and nerves within the patient's body which result in continued movement, or contraction, of the skin. Because the conductive fabric is a loose knit, stretching thereof does not deteriorate any of the conductive fibers therein to any substantial degree, thus causing loss of conductivity of the electrode.

In order to be effective in transmitting electrical signals to the patient's skin 20, the electrode 10 utilizes a conductive adhesive 24, such as one manufactured by Valley Lab, Inc., of Boulder, Colo., under the name Polyhesive, or Promeon RG-62D, manufactured by Promeon Corporation of Minneapolis, Minn. These proprietary products are useful in a number of electrode applications and have the advantage of being flexible so as to allow movement with the conductive fabric without losing contact with the patient's skin, or interrupting the electrical signals transmitted therethrough.

In the manufacture of the electrode 10, the conductive adhesive 24 is laminated as a gel or poured onto the surface 28 in a liquid form, whereupon it fills the interstitial areas 50 of the conductive fabric 22.

Thereafter, the adhesive is set into a gel-like material, which has good adhesion to the patient's skin, and is releasable therefrom without the annoyance of hair-pulling and the like. The conductive adhesive 24 is commercially available and is compatible with the skin in that it produces no irritation thereof.

Because the Polyhesive conductive adhesive 24 is in itself flexible, it does stretch with the conductive fabric between the interstitial areas 50 defined by the fibers 46.

Turning to FIGS. 2 and 3, the non-conductive plastic, or backing layer, 32 is adhered to the other side 36 of the conductive fabric 22, and both the backing layer and the pressure sensitive adhesive 38 hold the lead wire 30 in physical and electrical contact with the conductive fabric. In order to enhance contact therebetween, the conductive lead 30, which may be stranded stainless steel, having an end portion 54. The lead wire may have up to 1,159 strands of 8 micron diameter. Such wire is manufactured by Brunswick of DeLand, Fla.

In manufacture, the conductive lead is placed on the conductive fabric 22 for a distance of about one-third the length thereof. Thereafter, the backing layer 32, with adhesive 36 applied thereto, may be firmly placed over the frayed portion 60 and bonded by pressure applied thereto.

This relatively simple method of contacting the lead wire 30 with the conductive fabric 22 enables some movement therebetween as the conductive fiber and electrode stretch.

It should be appreciated that stretching along the direction 40, the major direction of stretch, may stretch the frayed strands 82 apart from one another, thus reducing the relative motion between the frayed end of 80 and the conductive fiber 22.

Because the conductive adhesive 24 is subject to drying, a release liner 52 may be provided for storage of the electrodes before and after use. This liner may be of any suitable plastic, or silicon-coated paper, which is strippable from the conductive adhesive 24 without disturbing the integrity of the conductive adhesive.

Figure 8:
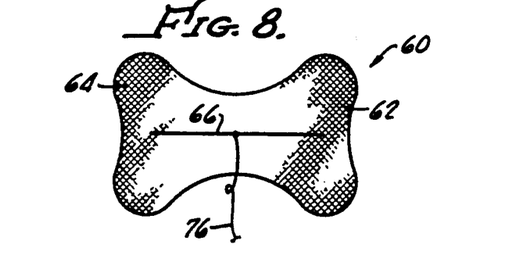
FIG. 8 is a plane view of a transcutaneous electrical nerve and/or muscle stimulation electrode in accordance with the present invention having an overall shape resembling a bow tie and showing an electrical shunt disposed thereon.

Turning now to FIG. 8, there is shown a flexible transcutaneous nerve and/or muscle stimulation electrode 60 in accordance with the present invention, which includes a conductive fabric 62 having an overall shape of a bow-tie, or butterfly, which is knit or woven with conductive fibers 64, as hereinbefore described. In addition, an electrical shunt 66 may be provided for causing more uniform resistance between any two equally spaced apart points on the conductive fabric 62 than without the electrical shunt means. When a knit fabric is utilized, the conductive fabric may have a higher resistivity along a longitudinal direction 42 of knit than along a transverse direction 40 of knit, see FIG. 4. This diversity in resistivity may amount to a factor of about 20.

Figure 9:
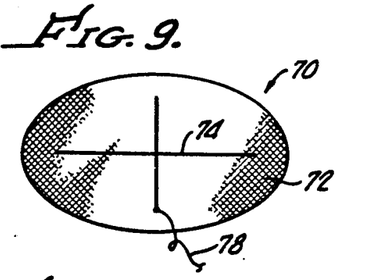
FIG. 9 is a plane view of a flexible transcutaneous electrical nerve and/or muscle stimulation electrode having an oval shape.
Figure 10:
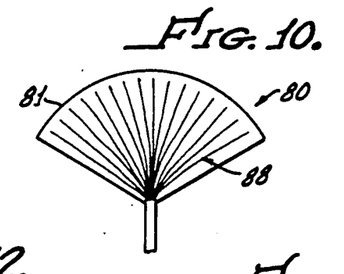
FIG. 10 is a plane view of a flexible transcutaneous electrical nerve and/or muscle stimulation electrode having an electrical shunt with strands disposed in a vein-like manner with dichotomous venation.
Figure 11:
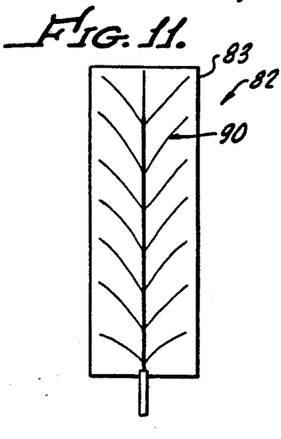
FIG. 11 is a plane view of a flexible transcutaneous electrical nerve and/or muscle stimulation electrode with pinnate reticulate venation.
Figure 12:
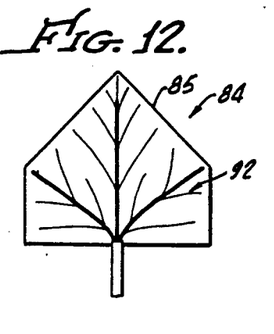
FIG. 12 is a plane view of a flexible transcutaneous electrical nerve and/or muscle stimulation electrode with palmate reticulate venation.
Figure 13:
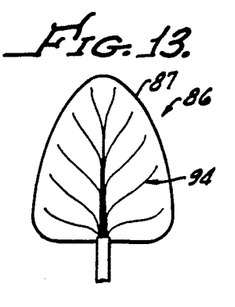
FIG. 13 is a plane view of a flexible transcutaneous electrical nerve and/or muscle stimulation electrode with parallel venation.

FIG. 9 shows an electrode 70 having a conductive fabric 72 with an overall oval shape and an electrical shunt 74 in the shape of a cross. The electrical shunt may comprise a plurality of strands, as for example, stainless wire having a diameter of about 8 microns. The shunt 66 and 74 are interconnected with lead wire 76, 78, respectively, for interconnection with an electrical stimulation device (not shown).

It should be appreciated that the shunt 66 and lead wire 76 may be continuous or separate stranded wires which are electrically connected. Another important feature of the T shunt shown in FIG. 8 is the fact that the orthogonal relationship between the shunt 66 and lead wire 76 provides greater resistance to the inadvertent "pulling out" of the lead wire due to abusive handling of the electrode by the lead wires. As hereinabove mentioned, the electrical shunt 66, 74 may be comprised of multiple strands in order to accommodate for variation in electrical resistivity of the fabric and, in addition, variation in electrical resistance between any two opposing points along the perimeter of the conductive fabric caused by a particular shape of the electrode.

The stranded shunt may be disposed in a vein-like pattern as shown in FIGS. 10, 11, 12 and 13, for various electrodes 80, 82, 84, 86, each having a particular venation of strands 88, 90, 92, 94, selected in order to cause equal resistance across the electrodes 80, 82, 84, 86. In particular, the venation shown in FIGS. 10, 11, 12 and 13 may be dichotomous, pinnate reticulate, palmate reticulate or parallel.

In addition, the strands 88, 90, 92, 94 may be terminated at a given distance from electrode edges 81, 83, 85, 87, calculated to increase the edge impedance in order to eliminate or substantially reduce the unwanted effect of high current density at the edges. This results in a smooth roll-off of stimulus intensity (and associated pain sensation) from electrode site on the user to non-stimulated surroundings.

It is to be appreciated that each of the strands 88, 90, 92, 94, which may be themselves single or multiple strands, may be electrically connected by simple overlaying of the strands with one another. The non-conductive plastic, or sheet 38 (see FIG. 3), holds the strands in position.

Typical fabric impedance are shown in Table 1 for various fabrics formed from the yarn having a 18 percent stainless steel and 82 percent polyester content. As can be determined therefrom, a woven fabric has an almost uniform impedance gradient along both the longitudinal and transverse directions. Unfortunately, it is not as flexible as knitted fabric and intends to fray, limiting its use to round shapes. The diamond knit fabric illustrated in FIG. 4, conducts about five times better in the transverse direction than int the longitudinal direction and a jersey knit fabric conducts 10 times better in the transverse direction than in the longitudinal direction. It should be appreciated than in a knitted fabric, the thread runs unbroken in the transverse direction. However, in the longitudinal direction, as the fabric comes off the knitting machine, electrical conduction is from thread to thread via knitted loops which give rise to the higher impedance. Thus, when conditions warrant the use of a knitted fabric for it s greater flexibility and variation in shape, the inherent non-uniform impedance thereof poses a problem in efforts to provide uniform electric field across the entire electrode.

TABLE 1

| FABRIC IMPEDANCE GRADIENTS | | | | |
|---|---|---|---|---|
| | Woven | Diamond Knit | Jersey Knit | Conductive Adhesive RG-62D |
| Longitudinal (Ohm*cm) X | 2.3 | 68.3 | 113.3 | 886.4 |
| Transverse (Ohm*cm) Y | 2.2 | 14.7 | 11.3 | 886.4 |
| X-Y Ratio | 1.0 | 4.6 | 10.0 | 1.0 |

Yarn: 18% Stainless Steel 82% Polyester

Figure 14A:
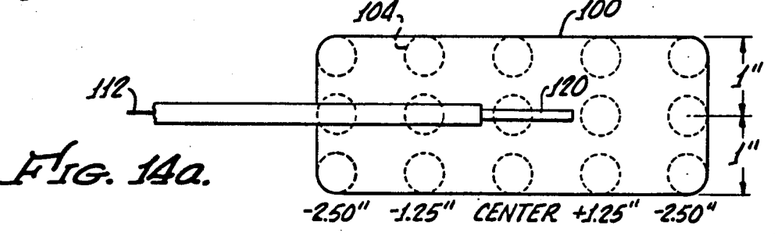
FIG. 14a and b are plane views of a 2 inch × 5 inch electrode each having different shunt lengths with impedance measurement portions shown thereon.
Figure 14B:
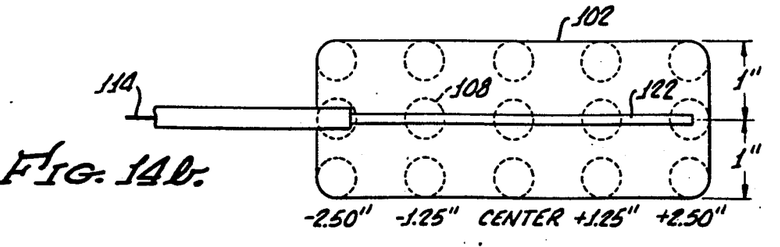
Figure 15:
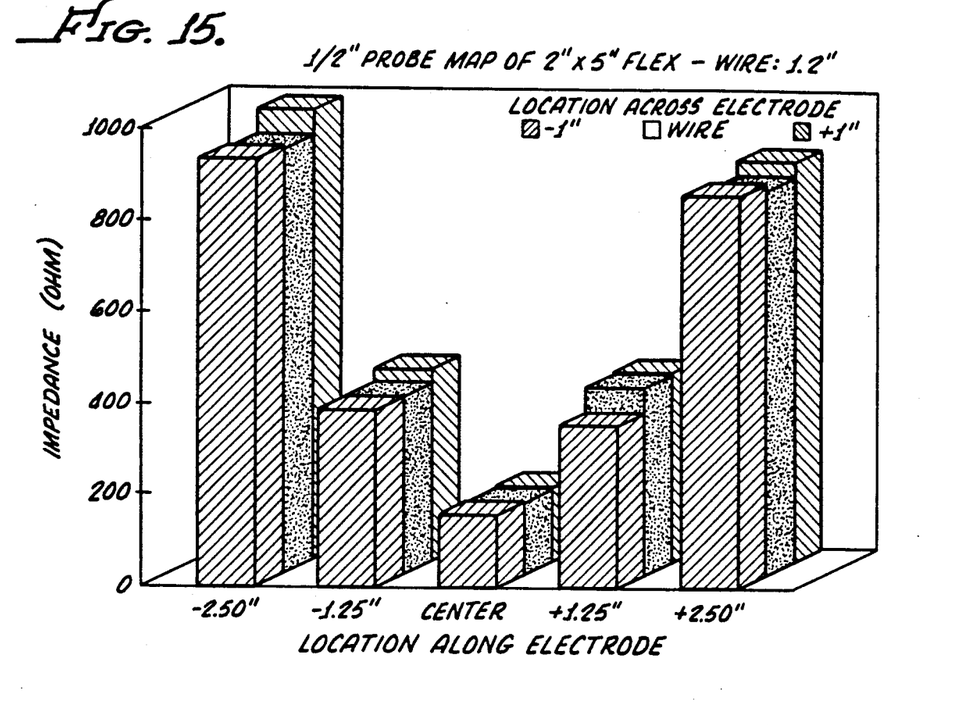
Figure 16:
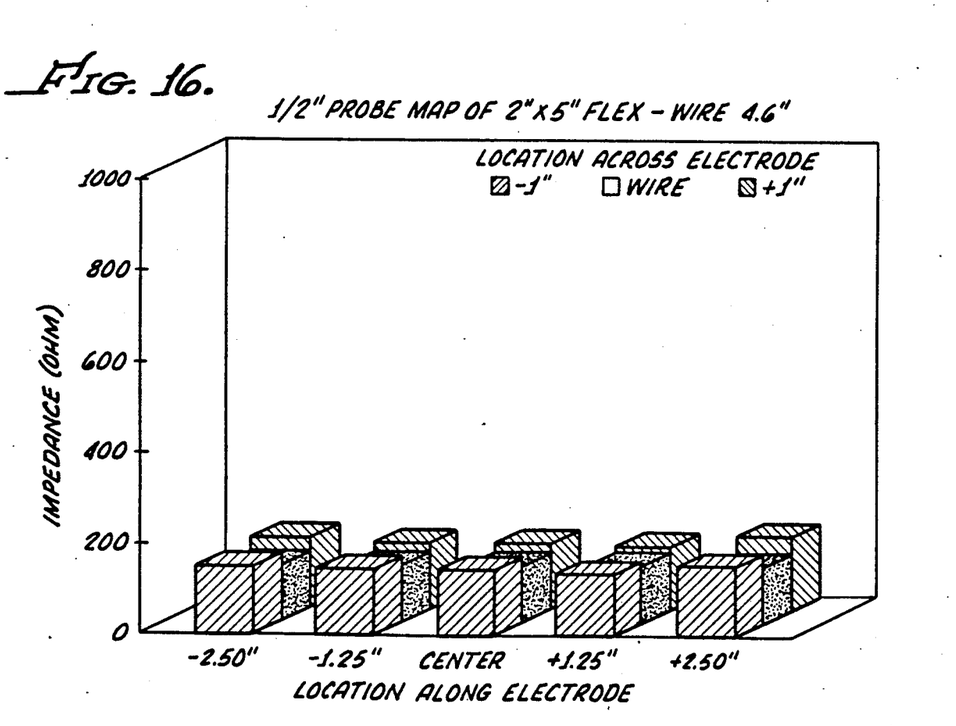
FIG. 16 is a probe map of the electrode shown in FIG. 14b.

FIG. 14a and 14b show 2×5 inch electrodes 100, 102, fabricated with jersey knit, the electrode 100 shown in FIG. 14a having a 1.2 inch exposed lead wire 120 and the electrode 102 shown in FIG. 14b having a 4.6 inch exposed lead wire 122. A ½ inch diameter probe was used to measure impedance from the conductive adhesive side between various positions 104, 108 and the wire 112, 114, respectively, and the results are shown in FIGS. 15 and 16 and numerically repeated in Tables 2 and 3.

TABLE 2

½" Probe Map of 2" × 5" JERSEY KNIT-WIRE: 1.2"

Waveform: Constant Current, Square Wave, DC-comp
 35 Hz, 200 usec, 30 mA
Probe: Flat, 7/16"
Electrode Data:  Dimension: 2" × 5"
  Lead Offset: 0
  Wire Exposed: 1-3/16
Gel: RG-62D

| Location Across Electrode | | Location Along Electrode | | | | |
|---|---|---|---|---|---|---|
| | | −2.50" | −1.25" | CEN-TER | +1.25" | +2.50" |
| −1" | Voltage | 29.0 | 12.0 | 5.1 | 11.0 | 26.0 |
| WIRE | Voltage | 28.0 | 12.0 | 5.0 | 12.4 | 25.5 |
| +1" | Voltage | 29.5 | 12.8 | 5.1 | 12.6 | 26.5 |
| −1" | Probe Imp | 956 | 389 | 159 | 356 | 856 |
| WIRE | Probe Imp | 922 | 389 | 156 | 402 | 839 |
| +1" | Probe Imp | 972 | 416 | 159 | 409 | 872 |
| −1" | El Imp | 57.4 | 23.4 | 9.6 | 21.4 | 51.4 |
| WIRE | El Imp | 55.4 | 23.4 | 9.4 | 24.2 | 50.4 |
| +1" | El Imp | 58.4 | 25.0 | 9.6 | 24.6 | 52.4 |

TABLE 3

½" Probe Map of 2" × 5" JERSEY KNIT-WIRE: 4.6"

Waveform: Constant Current, Square Wave, DC-comp
 35 Hz, 200 usec, 30 mA
Probe: Flat, 7/16"
Electrode Data:  Dimension: 2" × 5"
  Lead Offset: 0
  Wire Exposed: 4-5/8"
Gel: RG-62D

| Location Across Electrode | | Location Along Electrode | | | | |
|---|---|---|---|---|---|---|
| | | −2.50" | −1.25" | CEN-TER | +1.25" | +2.50" |
| −1" | Voltage | 4.8 | 4.7 | 4.7 | 4.4 | 5.0 |
| WIRE | Voltage | 4.0 | 4.0 | 4.0 | 4.0 | 4.0 |
| +1" | Voltage | 4.9 | 4.6 | 4.6 | 4.4 | 4.8 |
| −1" | Probe Imp | 149 | 146 | 146 | 136 | 156 |
| WIRE | Probe Imp | 122 | 122 | 122 | 122 | 122 |
| +1" | Probe Imp | 152 | 142 | 142 | 136 | 149 |
| −1" | El Imp | 9.0 | 8.8 | 8.8 | 8.2 | 9.4 |
| WIRE | El Imp | 7.4 | 7.4 | 7.4 | 7.4 | 7.4 |
| +1" | El Imp | 9.2 | 8.6 | 8.6 | 8.2 | 9.0 |

Figure 17:
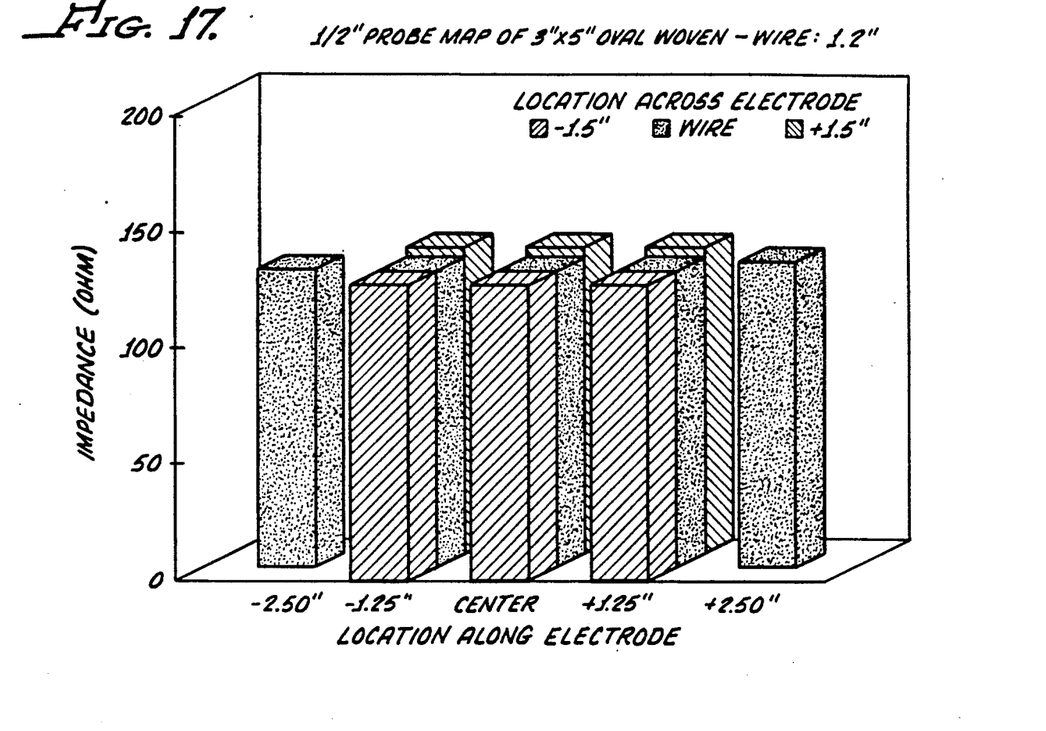
FIG. 17 is a probe map of an oval electrode with a 1.2 inch shunt.
Figure 18:
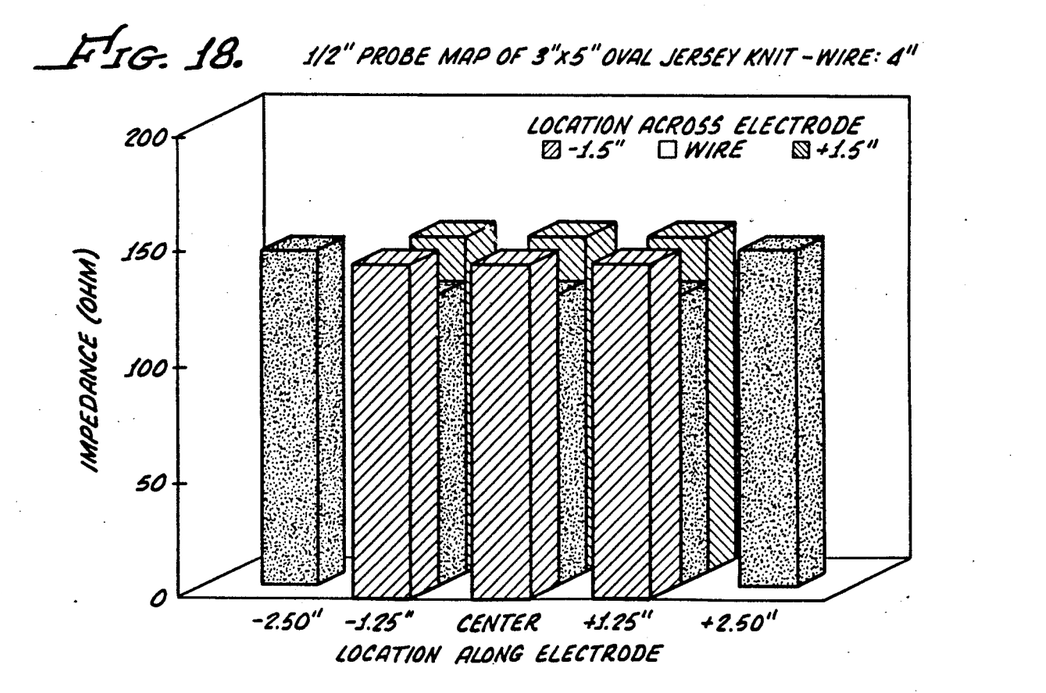
FIG. 18 is a probe map of an oval electrode with a 4 inch shunt.

It can be easily seen from an examination of FIGS. 15 and 16 that the extended shunt causes significantly greater uniformity in impedance across the entire surface of the electrode. Tables 4 and 5, corresponding FIGS. 17 and 18 show the impedance of an oval electrode, made in accordance with the present invention, utilizing a woven fabric with an exposed wire length of 1.2 inches and a jersey knit fabric with an exposed wire length of about 4 inches, respectively. As hereinabove pointed out, the woven fabric has an inherent uniform impedance gradient However, as set forth in Table 1, a jersey knit fabric does not. In accordance with the present invention, uniform impedance can be achieved utilizing the knit fabric as shown by the data in Tables 4 and 5 and corresponding plots shown in FIGS. 17 and 18.

It has been further discovered that uniform impedance may be achieved by both varying the length of exposed shunt wire to control the longitudinal impedance gradient and further, controlling the transverse impedance gradient by varying the ratio of stainless steel to polyester in the yarn, and by changing the knitting patterns. For example, the diamond knit shown in FIG. 4 has up to nine layers of yarn which result in approximately 5 to 1 X-Y impedance ratio, while a conventional jersey knit has only two layers giving it a 10 to 1 impedance ratio.

TABLE 4

½" PROBE MAP of 3" × 5" WOVEN OVAL FABRIC ELECTRODE-WIRE: 1.2"

Waveform: Constant Current, Square Wave, DC-comp 35 Hz, 200 usec, 30 mA
Probe: Flat, 7/16" diameter
Electrode Data:  Dimension:  3" × 5"
                 Lead Offset: 0
                 Wire Exposed: 1.2"
Total Electrode Impedance: 20 Ohm

| Location Across Electrode | −2.50" | −1.25" | CENTER | +1.25" | +2.50" |
|---|---|---|---|---|---|
| −1.5" Probe Imp |  | 127 | 127 | 127 |  |
| WIRE Probe Imp | 127 | 127 | 127 | 127 | 130 |
| +1.5" Probe Imp |  | 130 | 130 | 130 |  |

TABLE 5

½" PROBE MAP of 3" × 5" Oval JERSEY KNIT-WIRE: 4"

Waveform: Constant Current, Square Wave, DC-comp 35 Hz, 200 usec, 30 mA
Probe: Flat, 7/16" diameter
Electrode Data:  Dimension:  3" × 5"
                 Lead Offset: 0
                 Wire Exposed: 4"
Total Electrode Impedance: 12 Ohm

| Location Across Electrode | −2.50" | −1.25" | CENTER | +1.25" | +2.50" |
|---|---|---|---|---|---|
| −1.5" Probe Imp |  | 144 | 144 | 144 |  |
| WIRE Probe Imp | 144 | 124 | 124 | 124 | 144 |
| +1.5" Probe Imp |  | 144 | 144 | 144 |  |

Although hereinabove described in terms of knit or woven fabrics, the conductive fabric may also be any conductive material, such as for example, a conductive plastic. The present invention is particularly suited for use with conductive material having different electrical resistivity in different directions therealong. In this case, the use of shunts as hereinbefore described enables the fabrication of an electrode with uniform resistivity. Importantly, as shown in FIG. 18, the resistivity of an electrode can be tailored so that the current density across the electrode can taper, or decline, in a preselected manner to reduce or eliminate discomfort to the user due to large discontinuity in the edge current density as has been experienced by prior electrodes. (See Proceeding of IEEE Engineering in Medicine and Biology Society, Sept. 15-17, 1984, p. 187-190, Reddy, C. H. and Webster, J. G.).

Although there has been hereinabove described a specific arrangement of a flexible transcutaneous electrical nerve and/or muscle stimulation electrode in accordance with the invention for the purpose of illustrating the manner in which the invention may be used to advantage, it will be appreciated that the invention is not limited thereto. Accordingly, any and all modifications, variations, or equivalent arrangements which may occur to those skilled in the art, should be considered to be within the scope of the invention as defined in the appended claims.

What is claimed is:

1. A flexible transcutaneous electrical nerve and/or muscle stimulation electrode comprising:
   a conductive fabric comprising conductive fiber means for both enabling the conductive fabric to be stretched, and for directly coupling electrical signals to a patient's skin, said conductive fabric comprising an array of conductive fibers with interstitial areas therebetween, said conductive fabric having different electrical resistivity in different directions therealong;
   flexible solid conductive adhesive means disposed within said interstitial areas and on one side of said conductive fabric for both adhering the flexible transcutaneous electrical nerve and/or muscle stimulation electrode to the skin of a patient and providing an electrical conducting contact therebetween;
   electrical shunt means disposed along said conductive fabric for causing more uniform resistance between any two equally spaced apart points on said conductive fabric than without said electrical shunt means;
   electrical lead wire means interconnected with said electrical shunt means and adapted for interconnection with an electrical stimulation device for providing electrical signals to said conductive fabric; and,
   non-conductive sheet means disposed on another side of said conductive fabric for supporting the electrical shunt means along the conductive fabric and for preventing undesired electrical contact with the conductive fabric.

2. The flexible stimulation electrode according to claim 1 wherein said conductive fabric comprises a knit of conductive fibers having a higher resistivity along a longitudinal direction of knit than along a transverse direction of knit.

3. The flexible stimulation electrode according to claim 2 wherein the resistivity along the longitudinal direction of knit is up to about 20 times the resistivity along the transverse direction of knit.

4. The flexible stimulation electrode according to claim 1 wherein said electrical shunt means includes a plurality of strands disposed in a vein-like manner having a dichotomous venation.

5. The flexible stimulation electrode according to claim 1 wherein said electrical shunt means includes a plurality of strands disposed in a vein-like manner having a pinnate reticulate venation.

6. The flexible stimulation electrode according to claim 1 wherein said electrode shunt means includes a plurality of strands disposed in a vein-like manner having a palmate reticulate venation.

7. The flexible stimulation electrode according to claim 1 wherein said electrical shunt means includes a plurality of strands disposed in a vein-like manner having a parallel venation.

8. The flexible stimulation electrode according to claims 4, 5, 6 or 7 wherein said electrical shunt means is disposed on an opposite side of said conductive fabric and is held against said opposite side in an electrically conductive manner by the flexible solid conductive adhesive disposed in said interstitial area.

9. The flexible stimulation electrode according to claim 8 wherein said electrode shunt means comprises a plurality of strands of stainless steel wire having a diameter of about 8 microns.

10. A flexible transcutaneous electrical nerve and/or muscle stimulation electrode comprising:
   a conductive fabric comprising conductive fiber means for both enabling the conductive fabric to be stretched, and for directly coupling electrical signals to a patient's skin, said conductive fabric means comprising an array of conductive fibers with interstitial areas therebetween;
   means defining an overall shape of said conductive fabric for enabling improved conformity around and/or between body extremities than a conductive fabric having a shape selected from the group of square, rectangular and round, when the conductive fabric is adhered to said body extremities by an adhesive, said overall shape resulting in different electrical resistance between any two opposing points along a perimeter of said conductive fabric;
   electrical shunt means disposed along said conductive fabric for equalizing the electrical resistance between any two opposing points along the perimeter of said conductive fabric;
   flexible solid conductive adhesive means disposed within said interstitial areas and on one side of said conductive fabric for both adhering the flexible transcutaneous electrical nerve and/or muscle stimulation electrode to the skin of a patient and providing an electrical conducting contact therebetween;
   electrical lead wire means interconnected with said electrical shunt means and adapted for interconnection with an electrical stimulation device for providing electrical signals to said conductive fabric; and,
   non-conductive sheet means disposed on another side of said conductive fabric for supporting the electrical shunt means along he conductive fabric and for preventing undesired electrical contact with the conductive fabric.

11. The flexible stimulation electrode according to claim 10 wherein said conductive fabric has different electrical resistivity in different directions therealong and said electrical shunt means is disposed along said conductive fabric for causing more uniform resistance between any two equally spaced apart points on said conductive fabric than without said electrical shunt means.

12. The flexible stimulation electrode according to claim 10 wherein said electrical shunt means includes a plurality of strands disposed in a vein-like manner having a dichotomous venation.

13. The flexible stimulation electrode according to claim 10 wherein said electrical shunt means includes a plurality of strands disposed in a vein-like manner having a pinnate reticulate venation.

14. The flexible stimulation electrode according to claim 10 wherein said electrode shunt means includes a plurality of strands disposed in a vein-like manner having a palmate reticulate venation.

15. The flexible stimulation electrode according to claim 10 wherein said electrical shunt means includes a plurality of stands disposed in a vein-like manner having a parallel venation.

16. The flexible stimulation electrode according to claims 12, 13, 14 or 15 wherein said electrical shunt means is deposited on an opposite side of said conductive fabric and is held against said opposite side in an electrically conductive manner by the flexible solid conductive adhesive disposed in said interstitial areas.

17. The flexible stimulation electrode according to claim 16 wherein said electrical shunt means comprises a plurality of strands of stainless steel wire having a diameter of about 8 microns.

18. The flexible stimulation electrode according to claim 10 wherein said conductive fabric comprises a knit of conductive fibers having a higher resistivity along a longitudinal direction of knit than along a transverse direction of knit.

19. The flexible stimulation electrode according to claim 18 wherein the resistivity along the longitudinal direction of knit is up to about 20 times the resistivity along the transverse direction of knit.

20. The flexible stimulation electrode according to claim 10 wherein said conductive fabric overall shape comprises a bow-tie shape.

21. The flexible stimulation electrode according to claim 10 wherein said conductive fabric overall shape comprises an oval shape.

22. A flexible transcutaneous electrical nerve and/or muscle stimulation electrode comprising:
   a conductive knit fabric comprising conductive fiber means for both enabling the conductive fabric to be stretched, and for directly coupling electrical signals to a patient's skin, said conductive fabric comprising an array of conductive fibers with interstitial areas therebetween, said conductive fibers comprising a mixture of metallic and nonmetallic strands, said knit fabric having unbroken conductive fibers in a transverse direction along the fabric and joined conductive fibers in a longitudinal direction along the fabric;
   flexible solid conductive adhesive means disposed within said interstitial areas and on one side of said conductive fabric for both adhering the flexible transcutaneous electrical nerve and/or muscle stimulation electrode to the skin of a patient and providing an electrical conductive contact therebetween;
   electrical lead wire means interconnected with said conductive fabric and adapted for interconnection with an electrical stimulation device for providing electrical signals to said conductive fabric; and,
   non-conductive sheet means disposed on another side of said conductive fabric for supporting the electrical shunt means along the conductive fabric and for preventing undesired electrical contact with the conductive fabric.

23. The flexible stimulation electrode according to claim 22 wherein the unbroken conductive fibers comprises a lesser proportion of metallic strands than the joined conductive fibers.

24. The flexible stimulation electrode according to claim 23 wherein the metallic strands comprise stainless steel and the non-metallic strands comprise polyester.

25. The flexible stimulation electrode according to claim 24 wherein the stainless steel comprise between about 5 percent and about 25 percent of the total number of strands in each conductive fiber.

26. The flexible stimulation electrode according to claim 25 wherein the unbroken conductive fibers comprise about 10 percent to about 50 percent of the total number of strands therein and the joined conductive fibers comprises about 0 percent to about 25 percent of the total number of strands therein.

27. A flexible transcutaneous electrical nerve and/or muscle stimulation electrode comprising:
   means for coupling electrical signals to a patient's skin, said means comprising a conductive material;
   flexible solid conductive adhesive means disposed within a interstitial areas and on one side of said conductive material for both adhering the flexible transcutaneous electrical nerve and/or muscle stimulation electrode to the skin of a patient and providing an electrical conducting contact therebetween;
   electrical shunt means disposed along said conductive material for causing more uniform resistance between any two equally spaced apart points on said conductive material than without said electrical shunt means;
   electrical lead wire means interconnected with said electrical shunt means and adapted for interconnection with an electrical stimulation device for providing electrical signals to said conductive material; and,
   non-conductive sheet means disposed on another side of said conductive material for preventing undesired electrical contact with the conductive material.

28. The flexible stimulation electrode according to claim 27 wherein said conductive material has a different electrical resistivity in different directions therealong.

29. The flexible stimulation electrode according to claim 27 wherein said electrical shunt means includes a plurality of strands disposed in a vein-like manner having a dichotomous venation.

30. The flexible stimulation electrode according to claim 27 wherein said electrical shunt means includes a plurality of strands disposed in a vein-like manner having a pinnate reticulate venation.

31. The flexible stimulation electrode according to claim 27 wherein said electrode shunt means includes a plurality of strands disposed in a vein-like manner having a palmate reticulate venation.

32. The flexible stimulation electrode according to claim 27 wherein said electrical shunt means includes a plurality of strands disposed in a vein-like manner having a parallel venation.

33. The flexible stimulation electrode according to claims 1, 10 or 22, wherein said electrical shunt means is terminated a selected distance from an edge of the conductive fabric in order to reduce unwanted high current density at the conductive fabric edge.

34. The flexible stimulation electrode according to claim 27 wherein said electrode shunt means is terminated a selected distance from an edge of the conductive material in order to reduce unwanted high current density at the conductive material edge.

* * * * *